(12) United States Patent  (10) Patent No.: US 8,622,916 B2
Batchelder et al.  (45) Date of Patent: Jan. 7, 2014

(54) SYSTEM AND METHOD FOR FACILITATING OBSERVATION OF MONITORED PHYSIOLOGIC DATA

(75) Inventors: Keith Batchelder, New York, NY (US); Scott Amundson, Oakland, CA (US); Mark Brecht, Imperial Beach, CA (US)

(73) Assignee: Covidien LP, Mansfield, MA (US)

( * ) Notice: Subject to any disclaimer, the term of this patent is extended or adjusted under 35 U.S.C. 154(b) by 676 days.

(21) Appl. No.: 12/609,314

(22) Filed: Oct. 30, 2009

(65) Prior Publication Data

US 2010/0113909 A1    May 6, 2010

Related U.S. Application Data

(60) Provisional application No. 61/110,259, filed on Oct. 31, 2008.

(51) Int. Cl.
*A61B 5/02* (2006.01)
(52) U.S. Cl.
USPC ............................ 600/484; 600/529; 600/364
(58) Field of Classification Search
USPC .................................................. 600/323, 324
See application file for complete search history.

(56) References Cited

U.S. PATENT DOCUMENTS

| | | | |
|---|---|---|---|
| 3,638,640 A | 2/1972 | Shaw | |
| 4,936,679 A | 6/1990 | Mersch | |
| 4,971,062 A | 11/1990 | Hasebe et al. | |
| 4,974,591 A | 12/1990 | Awazu et al. | |
| 5,028,787 A | 7/1991 | Rosenthal et al. | |
| 5,065,749 A | 11/1991 | Hasebe et al. | |
| 5,084,327 A | 1/1992 | Stengel | |
| 5,275,159 A | 1/1994 | Griebel | |
| 5,483,646 A | 1/1996 | Uchikoga | |
| 5,730,124 A | 3/1998 | Yamauchi | |
| 5,779,631 A | 7/1998 | Chance | |
| 5,830,139 A | 11/1998 | Abreu | |
| 5,831,598 A | 11/1998 | Kauffert et al. | |

(Continued)

FOREIGN PATENT DOCUMENTS

| EP | 0615723 | 9/1994 |
|---|---|---|
| JP | 63275325 | 11/1988 |

(Continued)

OTHER PUBLICATIONS

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

(Continued)

*Primary Examiner* — Michael Kahelin
*Assistant Examiner* — Karen Toth

(57) ABSTRACT

Present embodiments are directed to a system and method capable of detecting and graphically indicating physiologic patterns in patient data. For example, present embodiments may include a monitoring system that includes a monitor capable of receiving input relating to patient physiological parameters and storing historical data related to the parameters. Additionally, the monitoring system may include a screen capable of displaying the historical data corresponding to the patient physiological parameters. Further, the monitoring system may include a pattern detection feature capable of analyzing the historical data to detect a physiologic pattern in a segment of the historical data and capable of initiating a graphical indication of the segment on the screen when the physiologic pattern is present in the segment.

20 Claims, 14 Drawing Sheets

(56) References Cited

U.S. PATENT DOCUMENTS

| | | | |
|---|---|---|---|
| 5,871,442 A | 2/1999 | Madarasz et al. | |
| 5,873,821 A | 2/1999 | Chance et al. | |
| 6,081,742 A | 6/2000 | Amano et al. | |
| 6,120,460 A | 9/2000 | Abreu | |
| 6,134,460 A | 10/2000 | Chance | |
| 6,285,895 B1 | 9/2001 | Ristolainen et al. | |
| 6,312,393 B1 | 11/2001 | Abreu | |
| 6,353,750 B1 | 3/2002 | Kimura et al. | |
| 6,415,236 B2 | 7/2002 | Kobayashi et al. | |
| 6,419,671 B1 | 7/2002 | Lemberg | |
| 6,461,305 B1 | 10/2002 | Schnall | |
| 6,487,439 B1 | 11/2002 | Skladnev et al. | |
| 6,544,193 B2 | 4/2003 | Abreu | |
| 6,549,795 B1 | 4/2003 | Chance | |
| 6,591,122 B2 | 7/2003 | Schmitt | |
| 6,606,509 B2 | 8/2003 | Schmitt | |
| 6,618,042 B1 | 9/2003 | Powell | |
| 6,622,095 B2 | 9/2003 | Kobayashi et al. | |
| 6,658,276 B2 | 12/2003 | Kiani et al. | |
| 6,662,030 B2 | 12/2003 | Khalil et al. | |
| 6,675,029 B2 | 1/2004 | Monfre et al. | |
| 6,687,519 B2 | 2/2004 | Steuer et al. | |
| 6,690,958 B1 | 2/2004 | Walker et al. | |
| 6,714,245 B1 | 3/2004 | Ono | |
| 6,731,274 B2 | 5/2004 | Powell | |
| 6,785,568 B2 | 8/2004 | Chance | |
| 6,793,654 B2 | 9/2004 | Lemberg | |
| 6,850,053 B2 | 2/2005 | Daalmans et al. | |
| 6,898,451 B2 | 5/2005 | Wuori | |
| 6,934,571 B2 | 8/2005 | Wiesmann et al. | |
| 6,949,081 B1 | 9/2005 | Chance | |
| 6,996,427 B2 | 2/2006 | Ali et al. | |
| 7,035,697 B1 | 4/2006 | Brown | |
| 7,041,063 B2 | 5/2006 | Abreu | |
| 7,043,289 B2 | 5/2006 | Fine et al. | |
| 7,065,392 B2 | 6/2006 | Kato | |
| 7,095,491 B2 | 8/2006 | Forstner et al. | |
| 7,186,966 B2 | 3/2007 | Al-Ali | |
| 7,236,811 B2 | 6/2007 | Schmitt | |
| 7,239,902 B2 | 7/2007 | Scmitt et al. | |
| 7,272,426 B2 | 9/2007 | Schmid | |
| 7,415,297 B2 | 8/2008 | Al-Ali et al. | |
| 7,469,158 B2 | 12/2008 | Cutler et al. | |
| 7,551,950 B2 | 6/2009 | Cheng | |
| 7,621,877 B2 | 11/2009 | Schnall | |
| 2002/0042558 A1 | 4/2002 | Mendelson | |
| 2002/0156354 A1 | 10/2002 | Larson | |
| 2002/0198443 A1 | 12/2002 | Ting | |
| 2003/0023140 A1 | 1/2003 | Chance | |
| 2004/0171920 A1 | 9/2004 | Mannheimer et al. | |
| 2005/0113651 A1 | 5/2005 | Wood et al. | |
| 2005/0113656 A1 | 5/2005 | Chance | |
| 2005/0192488 A1 | 9/2005 | Bryenton et al. | |
| 2005/0228248 A1 | 10/2005 | Dietiker | |
| 2006/0020181 A1 | 1/2006 | Schmitt | |
| 2006/0226992 A1 | 10/2006 | Al-Ali et al. | |
| 2006/0238358 A1 | 10/2006 | Al-Ali et al. | |
| 2006/0247501 A1 | 11/2006 | Ali | |
| 2006/0253010 A1 | 11/2006 | Brady et al. | |
| 2006/0258926 A1 | 11/2006 | Ali et al. | |
| 2007/0100218 A1 | 5/2007 | Sweitzer et al. | |
| 2007/0106132 A1 | 5/2007 | Elhag et al. | |
| 2007/0270665 A1 | 11/2007 | Yang et al. | |
| 2008/0076977 A1* | 3/2008 | Mannheimer et al. | 600/301 |
| 2008/0097175 A1* | 4/2008 | Boyce et al. | 600/323 |
| 2008/0208011 A1 | 8/2008 | Shuler | |
| 2008/0221418 A1* | 9/2008 | Al-Ali et al. | 600/324 |
| 2008/0234992 A1 | 9/2008 | Ray et al. | |
| 2008/0300474 A1 | 12/2008 | Benni et al. | |
| 2009/0209839 A1* | 8/2009 | Ochs et al. | 600/364 |

FOREIGN PATENT DOCUMENTS

| | | |
|---|---|---|
| JP | 2005034472 | 2/2005 |
| JP | 2006297125 | 11/2006 |
| WO | WO9316629 | 9/1993 |
| WO | WO9639927 | 12/1996 |
| WO | WO0021438 | 4/2000 |
| WO | WO0140776 | 6/2001 |
| WO | WO0176461 | 10/2001 |
| WO | WO0176471 | 10/2001 |
| WO | WO03039326 | 5/2003 |
| WO | 2006076498 A2 | 7/2006 |
| WO | WO 2006/076498 A1 * | 7/2006 |
| WO | 2007143535 A2 | 12/2007 |

OTHER PUBLICATIONS

East, Christine E., et al.; "Fetal Oxygen Saturation and Uterine Contractions During Labor," *American Journal of Perinatology*, vol. 15, No. 6, pp. 345-349 (Jun. 1998).

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Earthrowl-Gould, T., et al.; "Chest and abdominal surface motion measurement for continuous monitoring of respiratory function," *Proc. Instn Mech Engrs*, V215, Part H; pp. 515-520 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Yoon, Gilwon, et al.; Multiple diagnosis based on Photoplethysmography: hematocrit, SpO2, pulse and respiration, *Optics in Health Care and Biomedical optics: Diagnostics and Treatment; Proceedings of the SPIE*, vol. 4916; pp. 185-188 (2002).

A. Johansson; "Neural network for photoplethysmographic respiratory rate monitoring," *Medical & Biological Engineering & Computing*, vol. 41, pp. 242-248 (2003).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Australian Office Action in Application No. 2009308772 dated Jun. 12, 2012.

\* cited by examiner

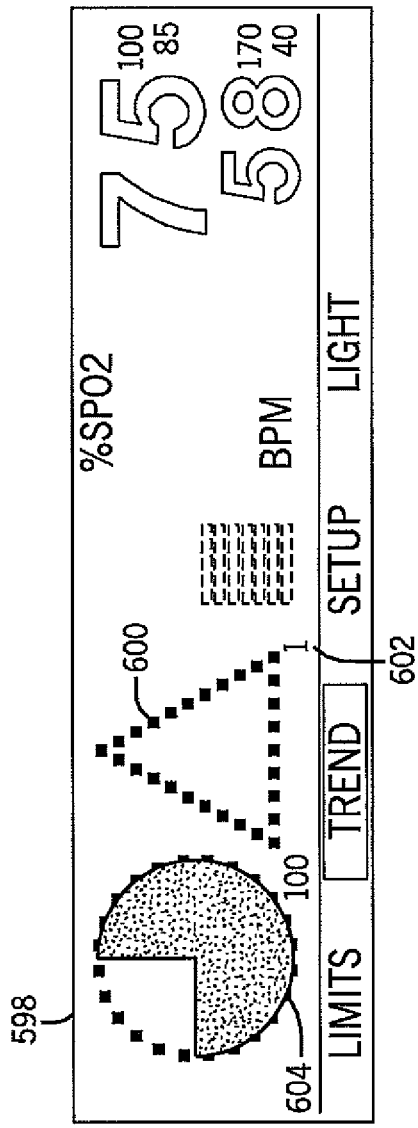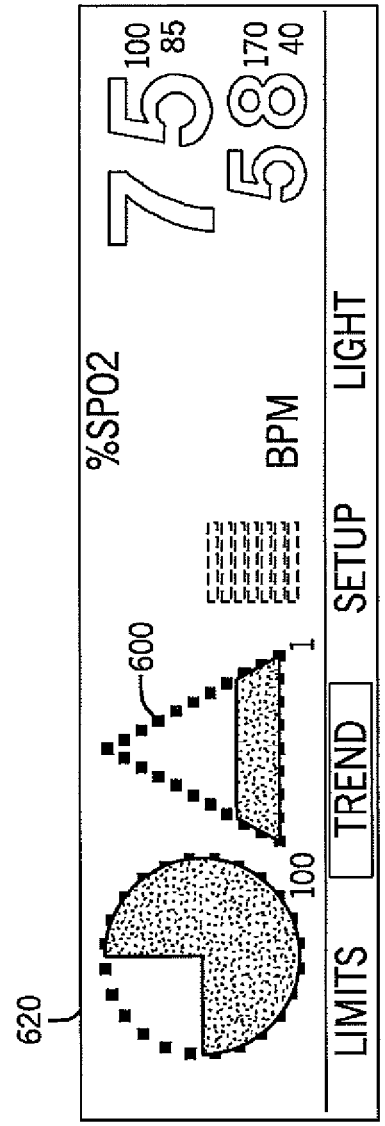

FIG. 17

```
800
┌─────────────────────────────┬──────────────┐
│ ALARMS                      │ %SPO2    100 │
│ ALLOW OFF?         [NO] YES │   ◯ △     85 │
│ OFF REMINDER?           YES │  100  3      │
│ ALLOW SAT-S             YES │ BPM      170 │
│                             │           40 │
├──────────────┬──────────────┼──────────────┤
│ SELECT   SPD │              │ BACK         │
└──────────────┴──────────────┴──────────────┘
```

FIG. 18

```
820
┌─────────────────────────────┬──────────────┐
│ SPD SETUP                   │ %SPO2 600100 │
│                             │   ◯ △     85 │
│ ALLOW SPD?         YES [NO] │  100  3      │
│ SPD AUDIO ALERT?            │ BPM      170 │
│                             │           40 │
├──────────────┬──────────────┼──────────────┤
│ SELECT       │ BACK         │ EXIT         │
└──────────────┴──────────────┴──────────────┘
```

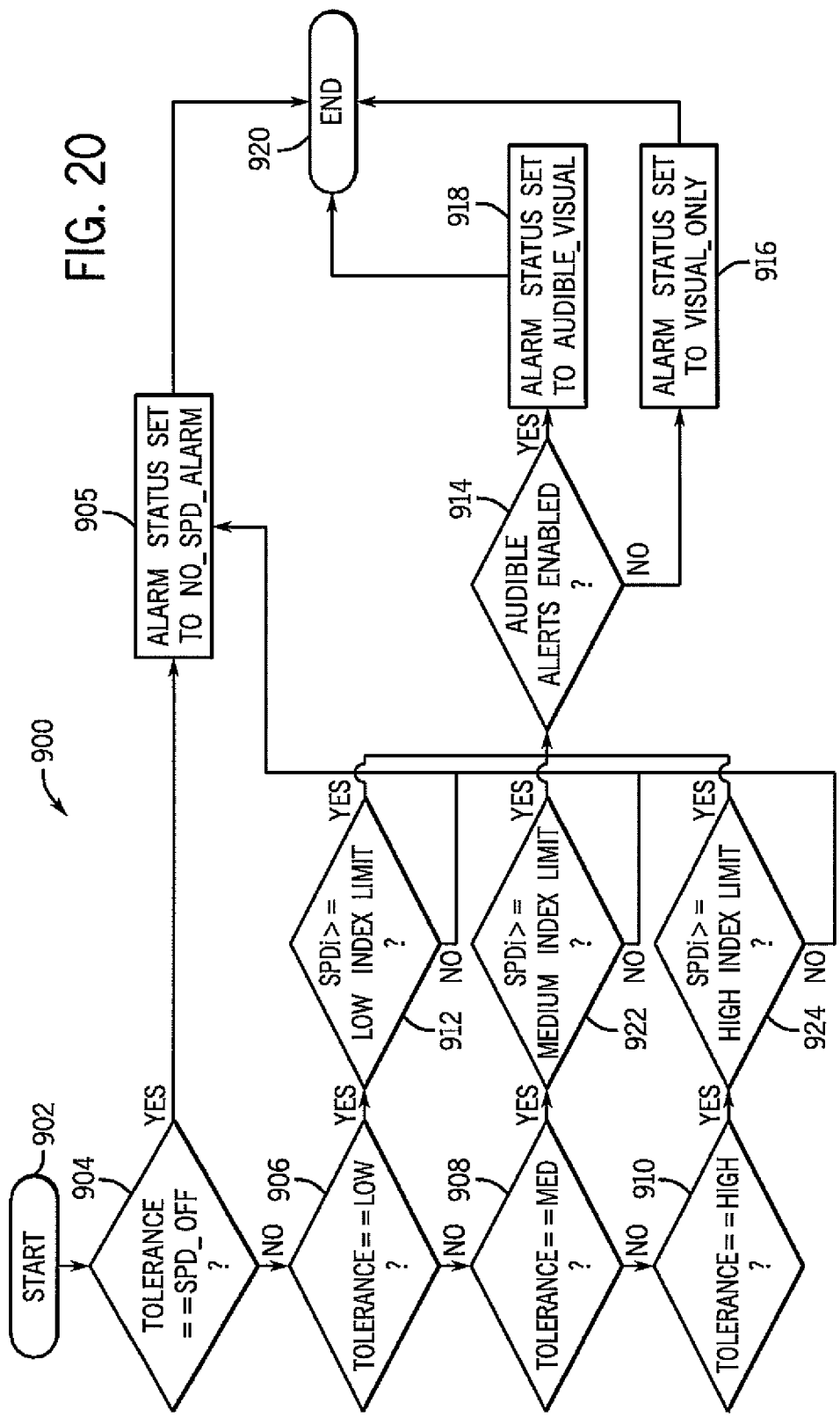

US 8,622,916 B2

SYSTEM AND METHOD FOR FACILITATING OBSERVATION OF MONITORED PHYSIOLOGIC DATA

RELATED APPLICATION

This application claims priority from U.S. Provisional Application No. 61/110,259 filed Oct. 31, 2008, which is hereby incorporated by reference herein in its entirety.

BACKGROUND

The present disclosure relates generally to user-interface applications for patient monitoring devices. In particular, present embodiments relate to display features that facilitate observation of monitored physiological data with patient monitoring instruments.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Patient monitors include medical devices that facilitate measurement and observation of patient physiological data. For example, pulse oximeters are a type of patient monitor. A typical patient monitor cooperates with a sensor to detect and display a patient's vital signs (e.g., temperature, pulse rate, or respiratory rate) and/or other physiological measurements (e.g., water content of tissue, or blood oxygen level) for observation by a user (e.g., clinician). For example, pulse oximeters are generally utilized with related sensors to detect and monitor a patient's functional oxygen saturation of arterial hemoglobin (i.e., $SpO_2$) and pulse rate. Other types of patient monitors may be utilized to detect and monitor other physiological parameters. The use of patient monitors may improve patient care by facilitating supervision of a patient without continuous attendance by a human observer (e.g., a nurse or physician).

A patient monitor may include a screen that displays information relating to operation and use of the patient monitor. A typical patient monitor screen may display patient data for further interpretation by a user. For example, a pulse oximetry monitor may display data in the form of a plethysmographic waveform or in the form of a numeric index, such as an oxygen saturation value. However, while a monitor may convey information to a user about the patient's condition, such information may be difficult to interpret quickly.

BRIEF DESCRIPTION OF THE DRAWINGS

Advantages of present embodiments may become apparent upon reading the following detailed description and upon reference to the drawings in which:

FIG. 7 is an exemplary display including a graphical indicator related to ventilatory instability;

FIG. 8 is an exemplary display including a graphical indicator related to ventilatory instability;

FIG. 17 is an exemplary display of a menu related to alarm management and settings for alarms related to ventilatory instability;

FIG. 18 is an exemplary display of a menu related to alarm management and settings for alarms related to ventilatory instability;

FIG. 20 is an exemplary flow chart of a process for alarm management for alarms related to ventilatory instability.

DETAILED DESCRIPTION

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments may facilitate observation of certain events (e.g., $SpO_2$ patterns) displayed on a monitor's user-interface by providing graphic indicators that relate to the status of certain features. Further, present embodiments may include one or more graphic features that are actively representative of a status of pattern detection or a level (e.g., a percentage of an alarm level) of a detected occurrence. Such graphic features may provide an active representation of a gradual build up of indicators that correspond to identification of a particular pattern or that are indicative of a severity level of an identified condition. Indeed, present embodiments may utilize an accumulation of data indicators to identify a physiologic pattern or a severity level of a particular event, and the graphic feature may gradually change as observed indications accumulate. For example, in accordance with embodiments, ventilatory instability may be detected when a number of certain data features have been detected within a time period. Thus, a percentage value associated with ventilatory instability detection may be identified by dividing the number of detected data features by the number utilized for identification of a ventilatory instability pattern, and the percentage may be represented in a dynamic graphic (e.g., a status bar). As a specific example, a graphic displayed as a triangle outline may gradually fill in the triangle outline from the bottom as certain indicators of a particular pattern accumulate. Thus, the triangle graphic may be completely filled in when the pattern is actually confirmed. Likewise, the triangle may empty when certain aspects are reduced. Similarly, a graphic may gradually fill or empty as certain severity thresholds or indexes of a particular event are reached.

Figure 1:
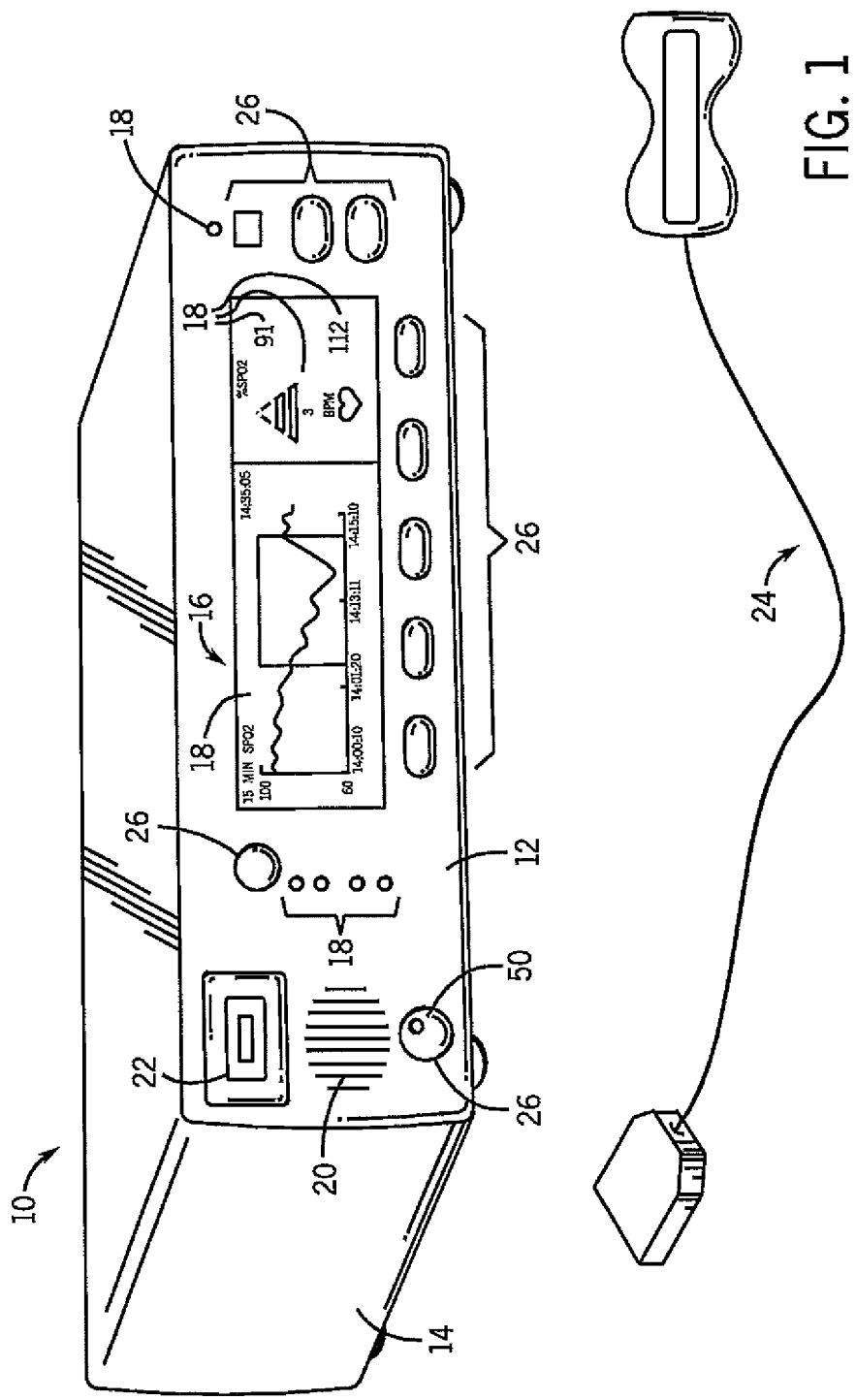
FIG. 1 is a perspective view of an exemplary patient monitor.

FIG. 1 is a perspective view of a patient monitor 10 in accordance with an exemplary embodiment of the present disclosure. Specifically, the patient monitor 10 illustrated by FIG. 1 is a pulse oximeter that is configured to detect and monitor blood oxygen saturation levels, pulse rate, and so forth. It should be noted that while the illustrated embodiment includes a pulse oximeter, other embodiments may include different types of patient monitors 10. For example, the patient monitor 10 may be representative of a vital signs monitor, a critical care monitor, an obstetrical care monitor, or the like.

The illustrated patient monitor 10 includes a front panel 12 coupled to a body 14 of the monitor 10. The front panel 12 includes a display screen 16 and various indicators 18 (e.g., indicator lights and display screen graphics) that facilitate operation of the monitor 10 and observation of a patient's physiological metrics (e.g., pulse rate). Some of the indicators 18 are specifically provided to facilitate monitoring of a patient's physiological parameters. For example, the indicators 18 may include representations of the most recently measured values for $SpO_2$, pulse rate, index values, and pulse amplitude. In embodiments, the indicators 18 may include an indicator related to ventilatory instability. In an embodiment, the indicator 18 may be a triangular indicator that is related to an index of ventilatory instability determined by the monitor 10. When the index increases, the triangle fills from bottom to top. In an embodiment, the indicator 18 may be a Sat Seconds indicator that provides an indication related to low oxygen saturation. Other indicators 18 may be specifically provided to facilitate operation of the monitor 10. For example, the indicators 18 may include an A/C power indicator, a low battery indicator, an alarm silence indicator, a mode indicator, and so forth. The front panel 12 may also include a speaker 20 for emitting audible indications (e.g., alarms), a sensor port 22 for coupling with a sensor 24 (e.g., a temperature sensor, a pulse oximeter sensor) and other monitor features.

Additionally, the front panel 12 may include various activation mechanisms 26 (e.g., buttons and switches) to facilitate management and operation of the monitor 10. For example, the front panel 12 may include function keys (e.g., keys with varying functions), a power switch, adjustment buttons, an alarm silence button, and so forth. It should be noted that in other embodiments, the indicators 18 and activation mechanisms 26 may be arranged on different parts of the monitor 10. In other words, the indicators 18 and activation mechanisms 26 need not be located on the front panel 12. Indeed, in some embodiments, activation mechanisms 26 are virtual representations in a display or actual components disposed on separate devices.

Figure 2:
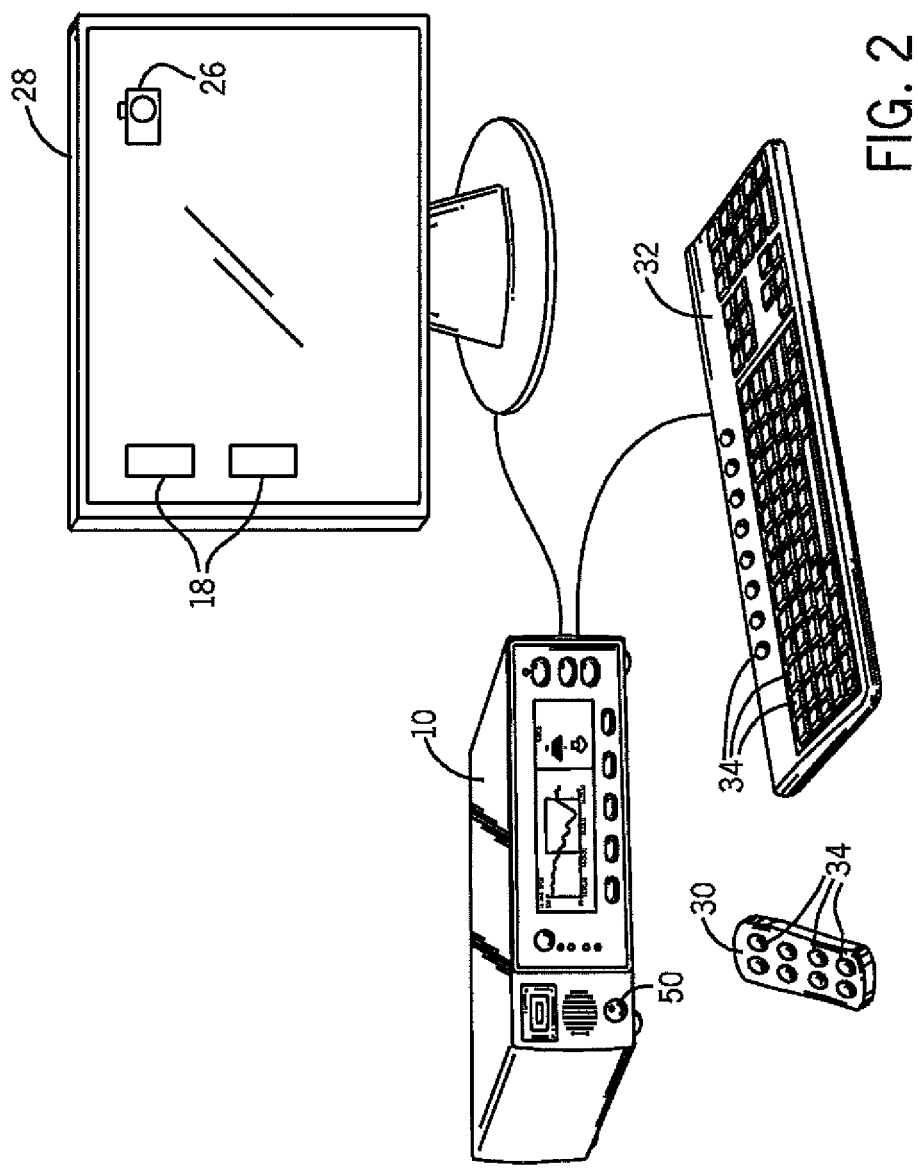
FIG. 2 is a perspective view of the exemplary patient monitor in a system with separate devices.

In some embodiments, as illustrated in FIG. 2, the monitor 10 may cooperate with separate devices, such as a separate screen 28, a wireless remote 30, and/or a keyboard 32. These separate devices may include some of the indicators 18 and activation mechanisms 26 described above. For example, buttons 34 on the remote 30 and/or keyboard 32 may operate as activation mechanisms 26. Specifically, for example, the buttons 34 may cause the monitor 10 to perform specific operations (e.g., power up, adjust a setting, silence an alarm) when actuated on the separate device. Similarly, the indicators 18 and/or activation mechanisms 26 may not be directly disposed on the monitor 10. For example, the indicators 18 may include icons, indicator lights, or graphics on the separate screen 28 (e.g., a computer screen). Further, the activation mechanisms 26 may include programs or graphic features that can be selected and operated via a display. It should be noted that the separate screen 28 and/or the keyboard 32 may communicate directly or wirelessly with the monitor 10.

Figure 3:
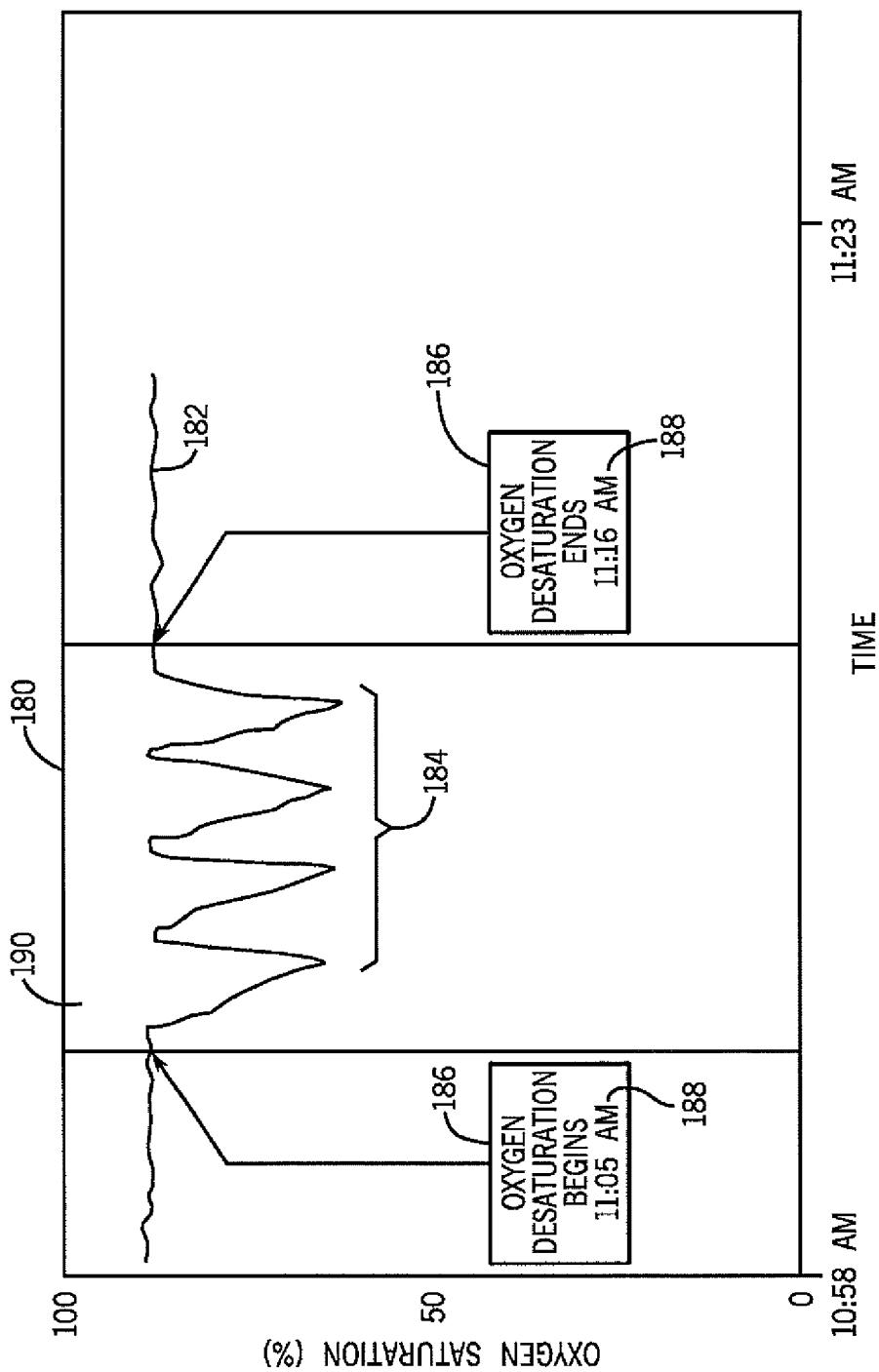
FIG. 3 is a representation of an exemplary display including a trend of physiological data that exhibits a detected pattern.

FIG. 3 is a representation of a display 180 that includes a trend 182 of oxygen saturation over time. As illustrated in FIG. 3, the monitor 10 may detect a cluster or pattern 184 of desaturation data, which the monitor 10 may determine is likely indicative of sleep apnea or some other issue. The monitor 10 may then label the pattern 184 with a textual graphic 186 and a timestamp 188 indicating a beginning and end of the detected pattern 184. Further, the monitor 10 may highlight or flash the pattern, as indicated by block 190, or utilize some other graphical indicator. In addition, the monitor may display an indicator that may provide information to a clinician that provides information that may be related to a patient condition. For example, the clinician may use present embodiments to simply snap or jump to a display including the pattern 184 (e.g., indication of sleep apnea or ventilation instability) by activating the display control feature (e.g., pressing a button), and the graphic indicators may draw the users attention to facilitate diagnosis.

Figure 4:
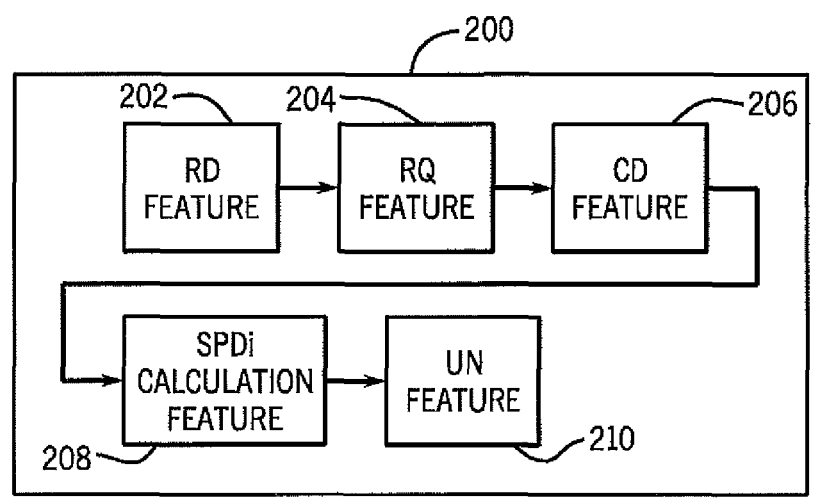
FIG. 4 is an exemplary block diagram of an electronic device.

In order to graphically or textually indicate the patterns in $SpO_2$ trend data (e.g., saturation patterns indicative of ventilatory instability), as discussed above, the patterns must first be detected. Accordingly, present embodiments may include code stored on a tangible, computer-readable medium (e.g., a memory) and/or hardware capable of detecting the presence of a saturation pattern in a series of physiologic data. For example, FIG. 4 is a block diagram of an electronic device or pattern detection feature in accordance with present embodiments. The electronic device is generally indicated by the reference number 200. The electronic device 200 (e.g., an $SpO_2$ monitor and/or memory device) may comprise various subsystems represented as functional blocks in FIG. 4. Those of ordinary skill in the art will appreciate that the various functional blocks shown in FIG. 4 may comprise hardware elements (e.g., circuitry), software elements (e.g., computer code stored on a hard drive) or a combination of both hardware and software elements. For example, each functional block may represent software code and/or hardware components that are configured to perform portions of an algorithm. Specifically, in the illustrated embodiment, the electronic device 200 includes a reciprocation detection (RD) feature 202, a reciprocation qualification (RQ) feature 204, a cluster determination (CD) feature 206, a saturation pattern detection index (SPDi) calculation feature 208, and a user notification (UN) feature 210. Each of these components and the coordination of their functions will be discussed in further detail below.

It should be noted that, in order to detect certain data patterns, embodiments of the present disclosure may utilize systems and methods such as those disclosed in U.S. Pat. No.

6,760,608, U.S. Pat. No. 6,223,064, U.S. Pat. No. 5,398,682, U.S. Pat. No. 5,605,151, U.S. Pat. No. 6,748,252, U.S. application Ser. No. 11/455,408 filed Jun. 19, 2006, U.S. application Ser. No. 11/369,379 filed Mar. 7, 2006, and U.S. application Ser. No. 11/351,787 filed Feb. 10, 2006. Accordingly, U.S. Pat. No. 6,760,608, U.S. Pat. No. 6,223,064, U.S. Pat. No. 5,398,682, U.S. Pat. No. 5,605,151, U.S. Pat. No. 6,748,252, U.S. application Ser. No. 11/455,408 filed Jun. 19, 2006, U.S. application Ser. No. 11/369,379 filed Mar. 7, 2006, and U.S. application Ser. No. 11/351,787 filed Feb. 10, 2006 are each incorporated herein by reference in their entirety for all purposes.

Figure 5:
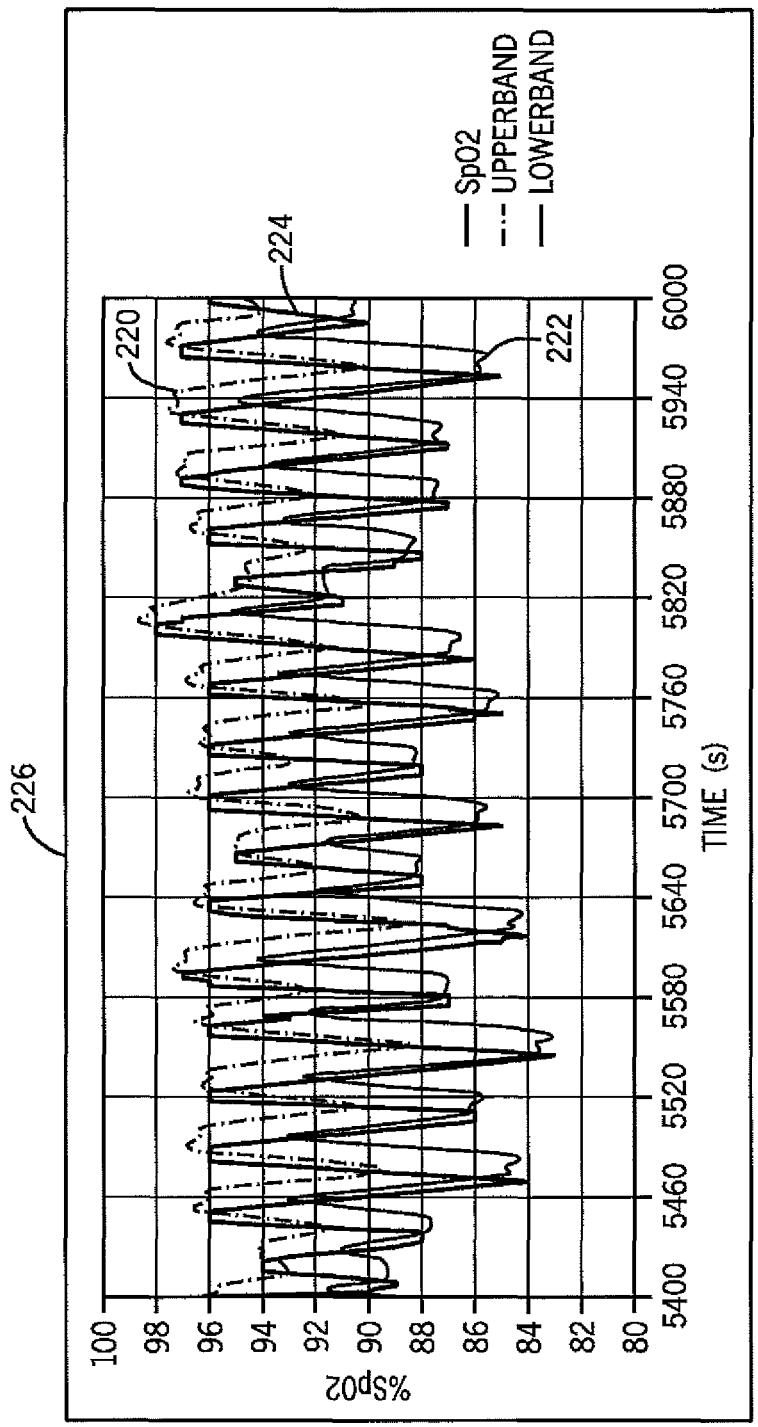
FIG. 5 is an exemplary graph of $SpO_2$ trend data with an upper band and lower band based on mean and standard deviation values.

The RD feature 202 may be capable of performing an algorithm for detecting reciprocations in a data trend. Specifically, the algorithm of the RD feature 202 may perform a statistical method to find potential reciprocation peaks and nadirs in a trend of $SpO_2$ data. A nadir may be defined as a minimum $SpO_2$ value in a reciprocation. The peaks may include a rise peak (e.g., a maximum $SpO_2$ value in a reciprocation that occurs after the nadir) and/or a fall peak (e.g., a maximum $SpO_2$ value in a reciprocation that occurs before the nadir). Once per second, the RD feature 202 may calculate a 12 second rolling mean and standard deviation of the $SpO_2$ trend. Further, based on these mean and standard deviation values, an upper band 220 and lower band 222 with respect to an $SpO_2$ trend 224, as illustrated by the graph 226 in FIG. 5, may be calculated as follows:

Upper Band=mean+standard deviation;

Lower Band=mean−standard deviation.

Once the upper band 220 and lower band 222 have been determined, potential reciprocation peaks and nadirs may be extracted from the $SpO_2$ trend 224 using the upper band 220 and the lower band 224. Indeed, a potential peak may be identified as the highest $SpO_2$ point in a trend segment which is entirely above the upper band 220. Similarly, a potential nadir may be identified as the lowest $SpO_2$ point in a trend segment that is entirely below the lower band 222. In other words, peaks identified by the RD feature 202 may be at least one standard deviation above the rolling mean, and nadirs identified by the RD feature 202 may be at least one standard deviation below the mean. If there is more than one minimum value below the lower band 222, the last (or most recent) trend point may be identified as a nadir. If more than one maximum value is above the upper band 220, the point identified as a peak may depend on where it is in relation to the nadir. For example, regarding potential peaks that occur prior to a nadir (e.g., fall peaks) the most recent maximum trend point may be used. In contrast, for peaks that occur subsequent to a nadir (e.g., rise peaks), the first maximum point may be used. In the example trend data represented in FIG. 5, a peak and nadir is detected approximately every 30-60 seconds.

In one embodiment, a window size for calculating the mean and standard deviation may be set based on historical values (e.g., average duration of a set number of previous reciprocations). For example, in one embodiment, a window size for calculating the mean and standard deviation may be set to the average duration of all qualified reciprocations in the last 6 minutes divided by 2. In another embodiment, an adaptive window method may be utilized wherein the window size may be initially set to 12 seconds and then increased as the length of qualified reciprocations increases. This may be done in anticipation of larger reciprocations because reciprocations that occur next to each other tend to be of similar shape and size. If the window remained at 12 seconds, it could potentially be too short for larger reciprocations and may prematurely detect peaks and nadirs. The following equation or calculation is representative of a window size determination, wherein the output of the filter is inclusively limited to 12-36 seconds, and the equation is executed each time a new reciprocation is qualified:

If no qualified reciprocations in the last 6 minutes:

Window Size=12(initial value)

else:

RecipDur=½*current qualified recip duration+½*previous RecipDur

Window Size=bound(RecipDur,12,36).

With regard to $SpO_2$ signals that are essentially flat, the dynamic window method may fail to find the three points (i.e., a fall peak, a rise peak, and a nadir) utilized to identify a potential reciprocation. Therefore, the RD feature 202 may limit the amount of time that the dynamic window method can search for a potential reciprocation. For example, if no reciprocations are found in 240 seconds plus the current adaptive window size, the algorithm of the RD feature 202 may timeout and begin to look for potential reciprocations at the current $SpO_2$ trend point and later. The net effect of this may be that the RD feature 202 detects potential reciprocations less than 240 seconds long.

Once potential peaks and nadirs are found using the RD feature 202, the RQ feature 204 may pass the potential reciprocations through one or more qualification stages to determine if a related event is caused by ventilatory instability. A first qualification stage may include checking reciprocation metrics against a set of limits (e.g., predetermined hard limits). A second qualification stage may include a linear qualification function. In accordance with present embodiments, a reciprocation may be required to pass through both stages in order to be qualified.

As an example, in a first qualification stage, which may include a limit-based qualification, four metrics may be calculated for each potential reciprocation and compared to a set of limits. Any reciprocation with a metric that falls outside of these limits may be disqualified. The limits may be based on empirical data. For example, in some embodiments, the limits may be selected by calculating the metrics for potential reciprocations from sleep lab data where ventilatory instability is known to be present, and then comparing the results to metrics from motion and breathe-down studies. The limits may then be refined to filter out true positives.

The metrics referred to above may include fall slope, magnitude, slope ratio, and path length ratio. With regard to fall slope, it may be desirable to limit the maximum fall slope to filter out high frequency artifact in the $SpO_2$ trend, and limit the minimum fall slope to ensure that slow $SpO_2$ changes are not qualified as reciprocations. Regarding magnitude, limits may be placed on the minimum magnitude because of difficulties associated with deciphering the difference between ventilatory instability reciprocations and artifact reciprocations as the reciprocation size decreases, and on the maximum magnitude to avoid false positives associated with sever artifact (e.g., brief changes of more than 35% $SpO_2$ that are unrelated to actual ventilatory instability). The slope ratio may be limited to indirectly limit the rise slope for the same reasons as the fall slope is limited and because ventilatory instability patterns essentially always have a desaturation rate that is slower than the resaturation (or recovery) rate. The path length ratio may be defined as Path Length/((Fall Peak−Nadir)+(Rise Peak−Nadir)), where Path Length=Σ|Current $SpO_2$ Value−Previous $SpO_2$ value| for all $SpO_2$ values in a reciprocation, and the maximum path length ratio may be limited to limit the maximum standard deviation of the reciprocation, which limits high frequency artifact. The following table (Table I) lists the above-identified metrics along with their associated equations and the limits used in accordance with one embodiment:

TABLE I

| Metric | Equation | Minimum | Maximum |
|---|---|---|---|
| Fall Slope | (Nadir − Fall Peak)/Time between Fall Peak and Nadir | −1.6 (Fast Response Mode) −1 (Normal Response Mode) | −0.08 (Fast Response Mode) −0.05 (Normal Response Mode) |
| Magnitude | Max(Rise Peak, Fall Peak) − Nadir | 3 | 35 |
| Slope Ratio | \|Fall Slope/Rise Slope\| | 0.05 | 1.75 |
| Path Length Ratio | Path Length = $\sum$\| Current SpO2 Value − Previous SpO2 Value\| for all SpO2 values in a Reciprocation. Path Length Ratio = Path Length/((Fall Peak − Nadir) + (Rise Peak − Nadir)) | N/A | 2 |

As indicated in Table I above, an oximetry algorithm in accordance with present embodiments may operate in two response modes: Normal Response Mode or Fast Response Mode. The selected setting may change the $SpO_2$ filtering performed by the oximetry algorithm, which in turn can cause changes in $SpO_2$ patterns. Therefore a saturation pattern detection feature may also accept a response mode so that it can account for the different $SpO_2$ filtering. Table I indicates values associated with both types of response mode with regard to the Fall Slope values.

A second qualification stage of the RQ feature 204 may utilize a object reciprocation qualification feature. Specifically, the second qualification stage may utilize a linear qualification function based on ease of implementation, efficiency, and ease of optimization. The equation may be determined by performing a least squares analysis. For example, such an analysis may be performed with MATLAB®. The inputs to the equation may include the set of metrics described below. The output may be optimized to a maximum value for patterns where ventilatory instability is known to be present. The equation may be optimized to output smaller values (e.g., 0) for other data sets where potential false positive reciprocations are abundant.

To simplify optimization, the equation may be factored into manageable sub-equations. For example, the equation may be factored into sub-equation 1, sub-equation D, and sub-equation 2, as will be discussed below. The output of each sub-equation may then be substituted into the qualification function to generate an output. The outputs from each of the sub-equations may not be utilized to determine whether a reciprocation is qualified in accordance with present embodiments. Rather, an output from a full qualification function may be utilized to qualify a reciprocation. It should be noted that the equations set forth in the following paragraphs describe one set of constants. However, separate sets of constants may be used based on the selected response mode. For example, a first set of constants may be used for the Normal Response Mode and a second set of constants may be used for the Fast Response Mode.

Preprocessing may be utilized in accordance with present embodiments to prevent overflow for each part of the qualification function. The tables (Tables II-VII) discussed below, which relate to specific components of the qualification function may demonstrate this overflow prevention. Each row in a table contains the maximum value of term which is equal to the maximum value of the input variable multiplied by the constant, wherein the term "maximum" may refer to the largest possible absolute value of a given input. Each row in a table contains the maximum intermediate sum of the current term and all previous terms. For example, a second row may contain the maximum output for the second term calculated, as well as the maximum sum of terms 1 and 2. It should be noted that the order of the row may match the order that the terms are calculated by the RQ feature 204. Further, it should be noted that in the tables for each sub-equation below, equations may be calculated using temporary signed 32-bit integers, and, thus, for each row in a table where the current term or intermediate term sum exceeds 2147483647 or is less than −2147483647 then an overflow/underflow condition may occur.

A first sub-equation, sub-equation 1, may use metrics from a single reciprocation. For example, sub-equation 1 may be represented as follows:

Eq1Score=SlopeRatio*$SrCf$+PeakDiff*$PdCf$+FallSlope*$FsCf$+PathRatio*$PrCf$+$Eq$1Offset, where SrCf, PdCf, FsCf, PrCf, and Eq1Offset may be selected using least squares analysis (e.g., using MATLAB®). PeakDiff may be defined as equal to |Recip Fall Peak−Recip Rise Peak|. It should be noted that PeakDiff is typically not considered in isolation but in combination with other metrics to facilitate separation. For example, a true positive reciprocation which meets other criteria but has a high peak difference could be an incomplete recovery. That is, a patient's $SpO_2$ may drop from a baseline to a certain nadir value, but then fail to subsequently recover to the baseline. However, when used in combination with other metrics in the equation, PeakDiff may facilitate separation of two classifications, as large peak differences are more abundant in false positive data sets.

With regard to sub-equation 1, the tables (Tables II and III) set forth below demonstrate that the inputs may be preprocessed to prevent overflow. Further, the tables set forth below include exemplary limits that may be utilized in sub-equation 1 in accordance with present embodiments. It should be noted that Table II includes Fast Response Mode constants and Table III includes Normal Response Mode constants.

TABLE II

| Term | Variable Type | Maximum Variable Value (a) | Variable Preprocessing | Constant Value (b) (Fast Mode) | Maximum Term Value (a * b) | Maximum Intermediate Sum (sum of all previous rows) | Overflow |
|---|---|---|---|---|---|---|---|
| PeakDiff*PdCf | U8 | 100 | None. This value may not exceed 100 since the maximum $SpO_2$ value accepted is 100 | −29282 | −2928200 | −2928200 | NO |

TABLE II-continued

| Term | Variable Type | Maximum Variable Value (a) | Variable Preprocessing | Constant Value (b) (Fast Mode) | Maximum Term Value (a * b) | Maximum Intermediate Sum (sum of all previous rows) | Overflow |
|---|---|---|---|---|---|---|---|
| SlopeRatio*SrCf | U8 | 255 | None | −1534 | −391170 | −3319370 | NO |
| FallSlope*FsCf | S16 | −32768 | None | −19 | 622592 | −2696778 | NO |
| PathRatio*PrCf | U16 | 65535 | None | −7982 | −523100370 | −525797148 | NO |
| Eq1Offset | N/A | N/A | N/A | 809250 | 809250 | −524987898 | NO |

TABLE III

| Term | Variable Type | Maximum Variable Value (a) | Variable Preprocessing | Constant Value (b) (Normal Mode) | Maximum Term Value (a * b) | Maximum Intermediate Sum (sum of all previous rows) | Overflow |
|---|---|---|---|---|---|---|---|
| PeakDiff*PdCf | U8 | 100 | None. This value may not exceed 100 since the maximum SpO2 value accepted is 100 | −33311 | −3331100 | −3331100 | NO |
| SlopeRatio*SrCf | U8 | 255 | None | −2151 | −548505 | −3879605 | NO |
| FallSlope*FsCf | S16 | −32768 | None | −706 | 23134208 | 19254603 | NO |
| PathRatio*PrCf | U16 | 65535 | None | −6178 | −404875230 | −385620627 | NO |
| Eq1Offset | N/A | N/A | N/A | 576330 | 576330 | −385044297 | NO |

A second sub-equation, sub-equation D, may correspond to a difference between two consecutive reciprocations which have passed the hard limit qualifications checks, wherein consecutive reciprocations include two reciprocations that are separated by less than a defined time span. For example, consecutive reciprocations may be defined as two reciprocations that are less than 120 seconds apart. The concept behind sub-equation D may be that ventilatory instability tends to be a relatively consistent event, with little change from one reciprocation to the next. Artifact generally has a different signature and tends to be more random with greater variation among reciprocations. For example, the following equation may represent sub-equation D:

EqD=SlopeRatioDiff*$SrDCf$+DurationDiff*$DDCf$+
NadirDiff*$NdCf$+
PathLengthRatioDiff*$PrDCf$_EqDOffset, where, SrDCf, DDCf, NdCf, PrDCf, and EqDOffset may be selected using least squares analysis (e.g., using MATLAB®). With regard to other variables in sub-equation D, SlopeRatioDiff may be defined as |Current Recip Slope Ratio−Slope Ratio of last qualified Recip|; DurationDiff may be defined as |Current Recip Duration−Duration of last qualified Recip|; NadirDiff may be defined as |Current Recip Nadir−Nadir value of last qualified Recip|; and PathLengthRatioDiff may be defined as |Current Recip Path Length Ratio−Path Length Ratio of last qualified Recip|.

With regard to sub-equation D, the tables (Tables IV and V) set forth below demonstrate that the inputs may be preprocessed to prevent overflow. Further, the tables set forth below include exemplary limits that may be utilized in sub-equation D in accordance with present embodiments. It should be noted that Table IV includes Fast Response Mode constants and Table V includes Normal Response Mode constants.

TABLE IV

| Term | Variable Type | Maximum Variable Value (a) | Variable Preprocessing | Constant Value (b) (Fast Mode) | Maximum Term Value (a * b) | Maximum Intermediate Sum (sum of all previous rows) | Overflow |
|---|---|---|---|---|---|---|---|
| EqDOffset | N/A | N/A | N/A | 885030 | 885030 | 885030 | NO |
| SlopeRatioDiff*SrDCf | U8 | 255 | None | −2809 | −716295 | 168735 | NO |
| DurationDiff*DDCf | U16 | 240 | The Recip detection module may only detect recips less than or equal to 240 seconds long | −2960 | −710400 | −541665 | NO |
| NadirDiff*NdCf | U8 | 100 | This value may not exceed 100 since the maximum SpO2 value accepted is 100 | −13237 | −1323700 | −1865365 | NO |
| PathLengthRatioDiff*PrDCf | U16 | 65535 | None | −7809 | −511762815 | −513628180 | NO |

TABLE V

| Term | Variable Type | Maximum Variable Value (a) | Variable Preprocessing | Constant Value (b) (Normal Mode) | Maximum Term Value (a * b) | Maximum Intermediate Sum (sum of all previous rows) | Overflow |
|---|---|---|---|---|---|---|---|
| EqDOffset | N/A | N/A | N/A | 847650 | 847650 | 847650 | NO |
| SlopeRatioDiff*SrDCf | U8 | 255 | None | −2629 | −670395 | 177255 | NO |
| DurationDiff*DDCf | U16 | 240 | The Recip detection module may only detect recips less than or equal to 240 seconds long | −4282 | −1027680 | −850425 | NO |
| NadirDiff*NdCf | U8 | 100 | This value may not exceed 100 since the maximum SpO2 value accepted is 100 | −11705 | −1170500 | −2020925 | NO |
| PathLengthRatioDiff*PrDCf | U16 | 65535 | None | −7844 | −514056540 | −516077465 | NO |

A third sub-equation, sub-equation 2, may combine the output of sub-equation D with the output of sub-equation 1 for a reciprocation (e.g., a current reciprocation) and a previous reciprocation. For example, the following equation may represent sub-equation 2:

Eq2Score=EqDScore*DCf+
    Eq1ScoreCurrent*CurrEq1Cf+
    Eq1ScorePrev*PrevEq1Cf, where DCf, N1Cf, PrevEq1Cf, and Eq2Offset may be selected using least squares analysis (e.g., using MAT-LAB®). With regard to other variables in sub-equation 2, EqDScore may be described as the output of sub-equation D; Eq1ScoreCurrent may be described as the output of sub-equation 1 for a current reciprocation; and Eq1ScorePrev may be described as the output of sub-equation 1 for the reciprocation previous to the current reciprocation.

With regard to sub-equation 2, the tables (Tables VI and VII) set forth below demonstrate that the inputs may be pre-processed to prevent overflow. Further, the tables set forth below include exemplary limits that may be utilized in sub-equation 2 in accordance with present embodiments. It should be noted that Table VI includes Fast Response Mode constants and Table VII includes Normal Response Mode constants.

TABLE VI

| Term | Variable Type | Maximum Variable Value (a) | Variable Preprocessing | Constant Value (b) (Fast Mode) | Maximum Term Value (a * b) | Maximum Intermediate Sum (sum of all previous rows) | Overflow |
|---|---|---|---|---|---|---|---|
| Eq2Offset | N/A | N/A | N/A | −203800 | −203800 | −203800 | NO |
| EqDScore*Dcf | S32 | −501590 | The largest output for sub-equation D may be −513628180 (see Table IV). The input value may be scaled by dividing the value by 1024. Therefore the largest input value may be −501590 | 529 | −265341110 | −265544910 | NO |
| Eq1ScorePrev*PrevEq1Cf | S32 | −512683 | The largest output for sub-equation 1 may be −524987898 (see Table II). The input value may be scaled by dividing the value by 1024. Therefore the largest input value may be −512683 | 333 | −170723439 | −436268349 | NO |
| Eq1ScoreCurrent*CurrEq1Cf | S32 | −512683 | Same as previous row | 617 | −316325411 | −752593760 | NO |

TABLE VII

| Term | Variable Type | Maximum Variable Value (a) | Variable Preprocessing | Constant Value (b) (Normal Mode) | Maximum Term Value (a * b) | Maximum Intermediate Sum (sum of all previous rows) | Overflow |
|---|---|---|---|---|---|---|---|
| Eq2Offset | N/A | N/A | N/A | −194550 | −194550 | −194550 | NO |
| EqDScore*DCf | S32 | −503981 | The largest output for sub-equation D may be −516077465 (see Table V). The input value may be scaled by dividing the value by 1024. Therefore the largest input value may be −503981 | 532 | −268117892 | −268312442 | NO |
| Eq1ScorePrev*PrevEq1Cf | S32 | −376000 | The largest output for sub-equation 1 may be −385024297 (see Table III). The input value may be scaled by dividing the value by 1024. Therefore the largest input value may be −376000 | 496 | −186496000 | −454808442 | NO |
| Eq1ScoreCurrent*CurrEq1Cf | S32 | −376000 | Same as previous row | 406 | −152656000 | −607464442 | NO |

A qualification function may utilize the output of each of the equations discussed above (i.e., sub-equation 1, sub-equation D, and sub-equation 2) to facilitate qualification and/or rejection of a potential reciprocation. For example, the output of the qualification function may be filtered with an IIR filter, and the filtered output of the qualification function may be used to qualify or reject a reciprocation. An equation for an unfiltered qualification function output in accordance with present embodiments is set forth below:

$$QF\text{Unfiltered} = Eq1Score*SingleRecipWt*Eq2Cf + N2Score*MultipleRecipWt*Eq2Cf + NConseeRecip*ConsecCf + RecipMax*MaxCf + \text{Artifact}\%*ArtCf + QF\text{Offset},$$

where Eq2Cf, ConsecCf, MaxCf, ArtCf, and QFOffset may be selected using least squares analysis (e.g., using MATLAB®), and, as indicated above, Eq1Score may be defined as the output of sub-equation 1.

Other metrics in the unfiltered qualification function include SingleRecipWt, MultipleRecipWt, NConsecRecip, RecipMax, and Artifact %. With regard to SingleRecipWt and MultipleRecipWt, when there are two or more consecutive qualified reciprocations (e.g., qualified reciprocations that are less than 120 seconds apart) present, SingleRecipWt may equal 0 and MultipleRecipWt may equal 1. However, when only a single reciprocation is present, SingleRecipWt may equal 1 and MultipleRecipWt may equal 0.

NConseRecip, which may be defined as equal to max(NConsecRecip',QFConsecMax), may include a count of the number of consecutive reciprocations (e.g., reciprocations that are less than or equal to 120 seconds apart) that have passed the hard limit checks. The value for NConsecRecip may be reset to 0 whenever a gap between any two partially qualified reciprocations exceeds 120 seconds. This may be based on the fact that ventilatory instability is a relatively long lasting event as compared to artifact. Therefore, as more reciprocations pass the hard limit checks, the qualification function may begin qualifying reciprocations that were previously considered marginal. However, to guard against a situation where something is causing a longer term artifact event (e.g., interference from nearby equipment), the value may be clipped to a maximum value to limit the metrics influence on the qualification function output.

RecipMax, which may be defined as equal to max(Fall Peak, Rise Peak), may facilitate making decisions about marginal reciprocations. Indeed, marginal reciprocations with higher maximum $SpO_2$ values may be more likely to get qualified than marginal reciprocations with lower $SpO_2$ values. It should be noted that this metric works in tandem with the NConsecRecip metric, and multiple marginal reciprocations with lower maximum $SpO_2$ values may eventually, over a long period of time, get qualified due to the NConsecRecip metric.

The metric Artifact % may be defined as an artifact percentage that is equal to 100*Total Artifact Count/Recip Duration, where Total Artifact Count is the number of times and artifact flag was set during the reciprocation. Present embodiments may include many metrics and equations that are used to set the artifact flag. Because of this it is a generally reliable indication of the amount of artifact present in the oximetry system as a whole. Marginal reciprocations with a high Artifact % are less likely to be qualified than marginal reciprocations with a low (or 0) artifact percentage.

A last component of the qualification function may include an infinite impulse response (IIR) filter that includes coefficients that may be tuned manually using a tool (e.g., a spreadsheet) that models algorithm performance. The filtered qualification function may be represented by the following equation, which includes different constants for different modes (e.g., Fast Response Mode and Normal Response Mode):

$$QF\text{Filtered} = SingleRecipWt*QF\text{Unfiltered} + ((1-a)*QF\text{Unfiltered} + a*\text{PrevQFFiltered})*MultipleRecipWt,$$

where QFUnfiltered may be defined as the current unfiltered qualification function output; PrevQFFiltered may be defined as the previous filtered qualification function output; and where the constat "a" may be set to 0.34 for Fast Response Mode and 0.5 for Normal Response Mode.

The filtered output of the qualification function may be compared to a threshold to determine if the current reciprocation is the result of RAF or artifact. The optimum threshold may theoretically be 0.5. However, an implemented threshold may be set slightly lower to bias the output of the qualification function towards qualifying more reciprocations, which may result in additional qualification of false positives. The threshold may be lowered because, in accordance with present embodiments, a cluster determination portion of the algorithm, such as may be performed by the CD feature 206, may require a certain number (e.g., 5) of fully qualified reciprocations before an index may be calculated, and a certain number (e.g., at least 2) of consecutive qualified reciprocations (with no intervening disqualified reciprocations) within the set of fully qualified reciprocations. Since multiple reciprocations may be required, the clustering detection method may be biased toward filtering out false positives. Accordingly, the reciprocation qualification function threshold may be lowered to balance the two processes.

The CD feature 206 may be capable of performing an algorithm that maintains an internal reciprocation counter that keeps track of a number of qualified reciprocations that are currently present. When the reciprocation counter is greater than or equal to a certain value, such as 5, the clustering state may be set to "active" and the algorithm may begin calculating and reporting the SPDi. When clustering is not active (e.g., reciprocation count <5) the algorithm may not calculate the SPDi. The SPDi may be defined as a scoring metric associated with the identification of a saturation trend pattern generated in accordance with present embodiment and may correlate to ventilatory instability in a population of sleep lab patients.

The CD feature 206 may utilize various rules to determine the reciprocation count. For example, when the clustering state is inactive, the following rules may be observed:

1.) If the distance between qualified reciprocation exceeds 120 seconds, then the reciprocation count=0;
2.) If the current reciprocation is qualified, and the time from the start of the current reciprocation to the end of the last qualified reciprocation is <=120 seconds, then the reciprocation count=reciprocation count+1;
3.) If the current reciprocation is not qualified, then the reciprocation count=max(reciprocation count−2, 0).

Once clustering is active, it may remain active until the time between two qualified reciprocations exceeds 120 seconds. The following table (Table II) illustrates an example of how the reciprocation count rules may be applied to determine a clustering state.

TABLE VIII

| Current Reciprocation Qualified | Time Since Last Qualified Reciprocation (seconds) | Reciprocation Count | Clustering State |
| --- | --- | --- | --- |
| TRUE | N/A | 1 | INACTIVE |
| FALSE | 60 | 0 | INACTIVE |
| TRUE | N/A | 1 | INACTIVE |
| FALSE | 60 | 0 | INACTIVE |
| TRUE | N/A | 1 | INACTIVE |
| TRUE | 30 | 2 | INACTIVE |
| TRUE | 120 | 3 | INACTIVE |
| FALSE | 60 | 1 | INACTIVE |
| TRUE | 10 | 2 | INACTIVE |
| TRUE | 20 | 3 | INACTIVE |
| TRUE | 40 | 4 | INACTIVE |
| FALSE | 30 | 2 | INACTIVE |
| FALSE | 60 | 0 | INACTIVE |
| TRUE | N/A | 1 | INACTIVE |
| TRUE | 20 | 2 | INACTIVE |
| TRUE | 120 | 3 | INACTIVE |
| TRUE | 10 | 4 | INACTIVE |
| FALSE | 90 | 2 | INACTIVE |
| TRUE | 120 | 3 | INACTIVE |
| TRUE | 60 | 4 | INACTIVE |
| TRUE | 20 | 5 | ACTIVE |
| TRUE | 30 | 6 | ACTIVE |
| FALSE | 50 | 6 | ACTIVE |
| FALSE | 100 | 6 | ACTIVE |
| TRUE | 121 | 1 | INACTIVE |
| FALSE | 50 | 0 | INACTIVE |
| TRUE | N/A | 1 | INACTIVE |
| TRUE | 30 | 2 | INACTIVE |
| TRUE | 121 | 1 | INACTIVE |
| TRUE | 10 | 2 | INACTIVE |
| TRUE | 20 | 3 | INACTIVE |
| TRUE | 40 | 4 | INACTIVE |
| TRUE | 40 | 5 | ACTIVE |

When the clustering state is active, the SPDi calculation feature 208 may calculate an unfiltered SPDi for each new qualified reciprocation. The following formula may be used by the SPDi calculation feature 208:

$$\text{Unfiltered SPDi} = a*\text{Magnitude} + b*\text{PeakDelta} + c*\text{NadirDelta};$$

wherein $a=1.4$, $b=2.0$, $c=0.2$;
wherein Magnitude=average magnitude of all reciprocations in the last 6 minutes;
wherein PeakDelta average of the three highest qualified reciprocation rise peaks in the last 6 minutes minus the average of the three lowest qualified reciprocation rise peaks in the last 6 minutes; and
wherein NadirDelta=average of the three highest qualified reciprocation nadirs in the last 6 minutes minus the average of the three lowest qualified reciprocation nadirs in the last 6 minutes.
Wherein SPDi<=31

The above formula may be utilized to quantify the severity of a ventilatory instability pattern. The constants and metrics used may be based on input from clinical team members. It should be noted that the PeakDelta parameter may be assigned the largest weighting constant since the most severe patterns generally have peak reciprocation values that do not recover to the same baseline.

The unfiltered SPDi may be updated whenever clustering is active and a new qualified reciprocation is detected. Non-zero SPDi values may be latched for a period of time (e.g., 6 minutes). The unfiltered SPDi may then be low pass filtered to produce the final output SPDi value. The following IIR filter with a response time of approximately 40 seconds may be used:

$$SPDi = \text{Unfiltered } SPDi/a + \text{Previous Filtered } SPDi*(a-1)/a;$$

wherein $a=40$.

Figure 6:
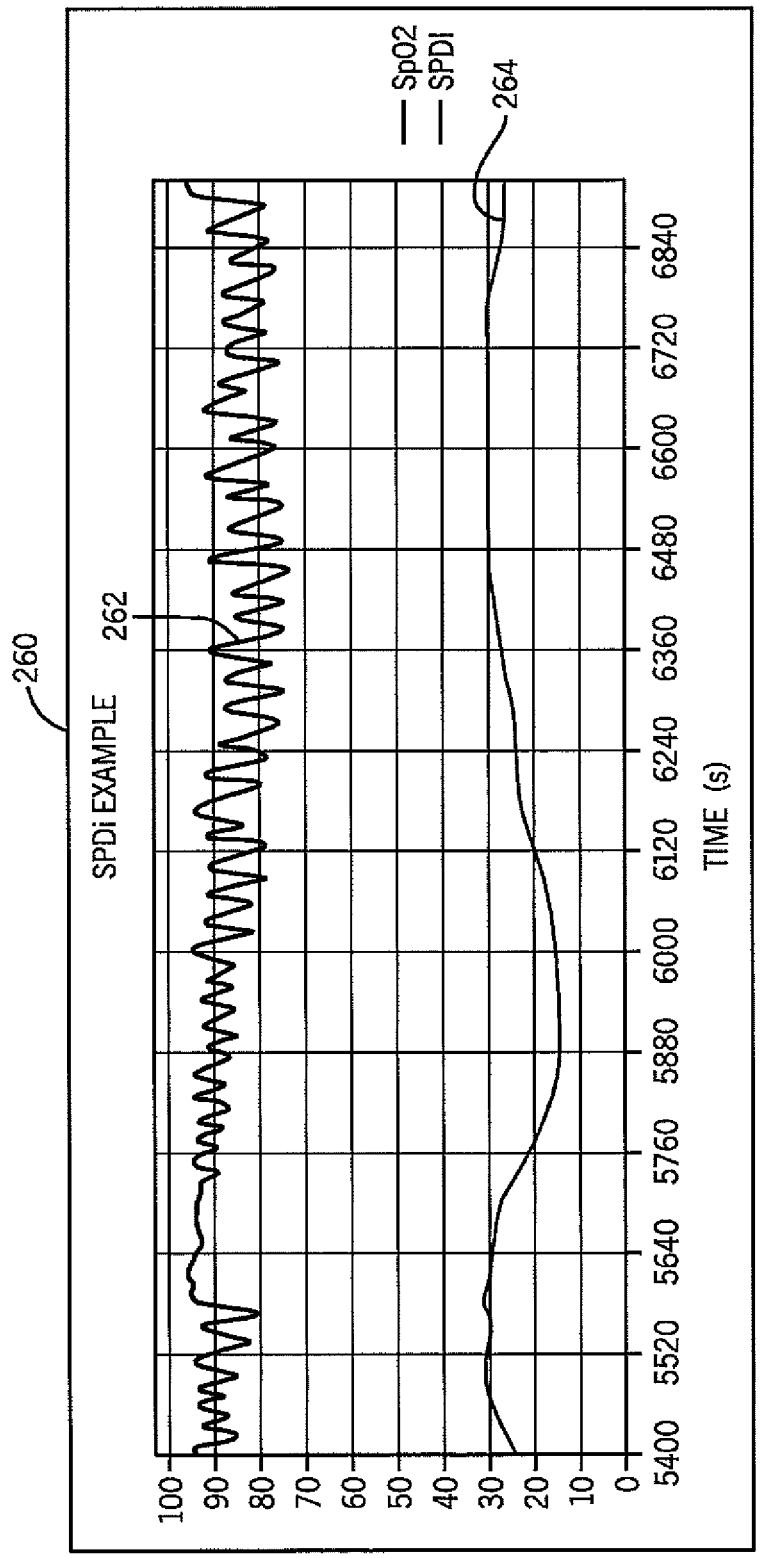
FIG. 6 is an exemplary graph including an $SpO_2$ trend that contains a ventilatory instability $SpO_2$ pattern and a trend of the resulting saturation pattern detection index.

FIG. 6 is an exemplary graph 260 including an $SpO_2$ trend 262 that contains a ventilatory instability $SpO_2$ pattern and a trend of the resulting SPDi 264. In the illustrated example, it should be noted that the SPDi is sensitive to the decreasing peaks (incomplete recoveries) starting at approximately t=6000.

The UN feature 210 may be capable of determining if a user notification function should be employed to notify a user (e.g., via a graphical or audible indicator) of the presence of a detected patterns such as ventilatory instability. The determination of the UN feature 210 may be based on a user configurable tolerance setting and the current value of the SPDi. For example, the user may have four choices for the sensitivity or tolerance setting: Off, Low, Medium, and High. When the sensitivity or tolerance setting is set to Off, an alarm based on detection of a saturation pattern may never be reported to the user. The other three tolerance settings (i.e., Low, Medium, and High) may each map to an SPDi threshold value. For example, Low may map to an SPDi threshold of 6, Medium may map to an SPDi threshold of 15, and High may map to an SPDi threshold of 24. The thresholds may be based on input from users. When the SPDi is at or above the threshold for a given tolerance setting, the user may be notified that ventilatory instability is present. As discussed below, the indication to the user may include a graphical designation of the trend data corresponding to the detected pattern. For example, the trend data utilized to identify a ventilatory instability pattern may be highlighted, flashing, or otherwise indicated on a user interface of a monitor in accordance with present embodiments. Similarly, parameters such as the SPDi value and the tolerance settings may be graphically presented on a display.

In embodiments, the display may include a graphical indicator that may provide information to a user related to the occurrence, frequency, and/or magnitude of the patterns detected. The information may be based on the SPDi index, which is proportional to the magnitude and variability of qualified reciprocations. The SPD calculation feature may be capable of notifying a user of ventilatory instability that corresponds to a certain SPDi index value. In embodiments, when the SPDi is at or above a threshold setting, the user may be notified via a graphical indicator 600.

Figure 9:
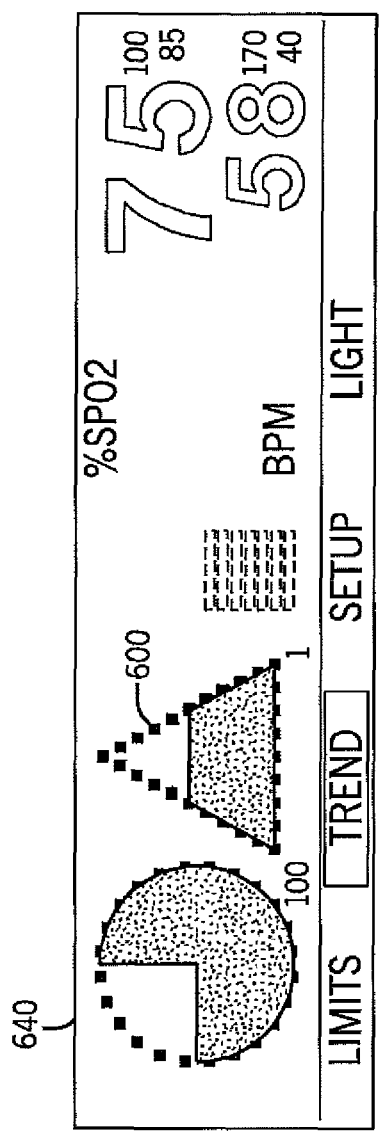
FIG. 9 is an exemplary display including a graphical indicator related to ventilatory instability.

As illustrated in FIG. 7, the graphical indicator 600 may be represented on display 598 as a dashed triangle that may graphically fill from top to bottom as a monitored and/or calculated value increases. For example, in one embodiment, the graphical indicator 600 may gradually fill as the SPDi index calculated by the SPDi calculation feature 208 increases. Further, the graphical indicator 600 may include a tolerance level indicator 602 that displays an index, for example 1, 2, or 3, for tolerance or sensitivity settings of High, Medium, and Low, respectively, for the SPDi calculation feature 208. The tolerance settings may set the threshold for triggering a change in the graphical indicator 600 and/or for triggering SPD-associated alarms. As shown in FIG. 9, the graphical indicator 600 may be empty, indicating that an SPDi index is below a certain threshold.

In addition, the display 598 may also include additional indicators, such as a Sat Seconds indicator 604 that relates to oxygen saturation information. Sat Seconds indicators may assist clinicians in focusing on desaturations related to a patient condition rather than short desaturations that may be the result of measurement anomalies. As shown, the Sat Seconds indicator 604 may be partially full while the graphical indicator 600 is empty. The Sat Seconds indicator 604 may display results determined by a Sat Second analyzing function, which in an embodiment analyzes desaturation events by multiplying their duration (seconds) by the number of percentage points the patient exceeds the alarm limit. In an embodiment, the Sat Seconds analyzer may determine if an oxygen desaturation event has occurred by analyzing a plot of oxygen saturation versus time. The Sat Seconds analyzer may integrate the area under the curve of time spent below a certain oxygen saturation threshold. Accordingly, sudden, short desaturation readings that may be measurement noise (e.g., that otherwise may trigger nuisance alarms) may be eliminated from a Sat Seconds counter clock while more prolonged desaturations may be counted. Clinicians can set the SatSeconds limit, or clock, to 10, 25, 50 or 100 SatSeconds. In an embodiment, the clock may be set to 100, and therefore only events that equal or surpass the 100 SatSeconds limit may trigger an alarm. In addition, the Sat Seconds indicator 604 may fill up in relation to the Sat Seconds count. For example, the indicator 604 may be full when the count reaches 100.

While the Sat Seconds indicator 604 may manage nuisance alarms related to desaturation events, the graphical indicator 600 may display information determined by not only the duration and magnitude of the oxygen desaturation, but also to the patterns of the desaturation events, as provided herein. Such analysis may provide information to the healthcare provider about ventilatory instability that may, for example, be related to sleep apnea. Turning to the graphical indicator 600, which provides information to a clinician related to ventilatory instability, FIG. 8 shows a display screen 620 in which the graphical indicator 600 has started to fill up from the bottom. The "filling up" may represent the addition of a fill (e.g., any color pixels) to the area of the triangle. In one embodiment, the graphical indicator 600 may fill up when the calculated SPDi index is higher than a tolerance setting. As noted, the High Tolerance, Medium Tolerance, and Low Tolerance alarm limits may refer to certain default values of the SPDi index, such as 24, 15, and 6, respectively. When the SPDi index is higher than, for example, 24 (High Tolerance setting), the graphical indicator 600 may begin to fill. In an embodiment, the graphical indicator 600 may begin to fill up when the SPDi index is lower than but near 24, whereby an SPDi index of 24 represents a "full" state. In such an embodiment, the approximately 25% full graphical indicator as shown may represent an SPDi index of, for example, 18.

FIG. 9 is a display 640 including an indicator 600 that is approximately 50% full. As noted, the graphical indicator 600 may continue to fill as the SPDi index rises over time. The SPDi index may be calculated over a rolling period of time. In embodiments, the SPDi index may be calculated over a 240 second window. If, during this window of time, the SPDi index increases as a result an increase in measured recip frequency or magnitude parameters used to determine the index, the graphical indicator 600 may continue to fill up.

Figure 10:
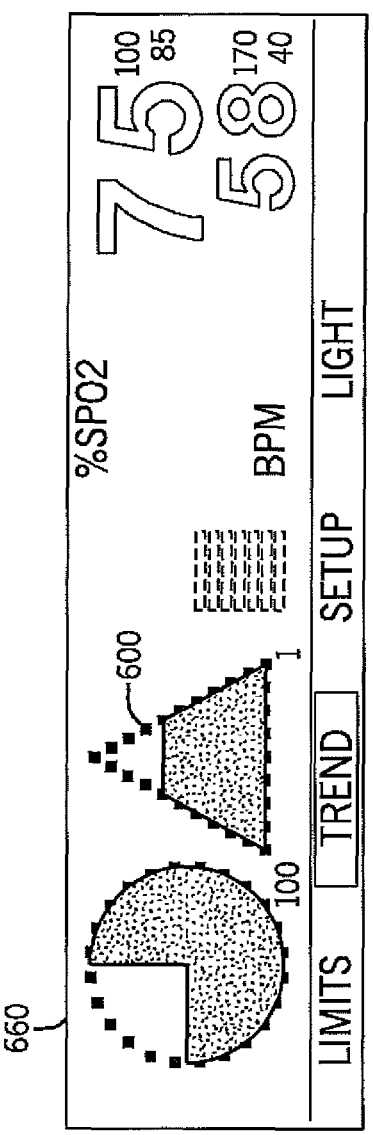
FIG. 10 is an exemplary display including a graphical indicator related to ventilatory instability.
Figure 11:
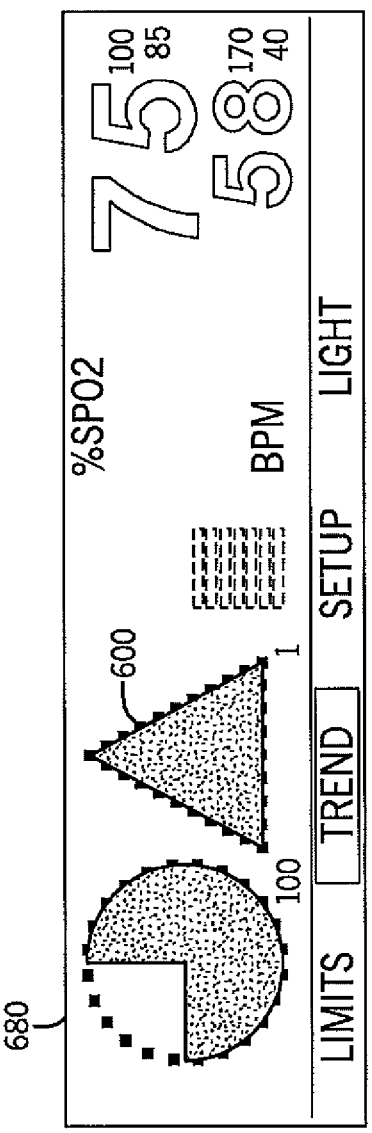
FIG. 11 is an exemplary display including a graphical indicator related to ventilatory instability.

FIG. 10 is an exemplary display 660 showing a graphical indicator 600 that is approximately 75% full, and FIG. 11 is an exemplary display 680 showing a graphical indicator 600 that is approximately 100% full. As shown in FIGS. 7-11, the indicator 600 may fill up as a percentage or fraction of the total indicator space as the SPDi index increases. For example, the indicator 600 may have five possible display states: empty, 25% full, 50% full, 75% full, or 100% full. In embodiments, the indicator 600 may fill in any suitable manner. For example, a graphical indicator may have any number of fill states, e.g., filling up in 10%, 20%, 25%, or 50% increments. In other embodiments, the indicator 600 may also change in intensity to indicate increasing ventilatory instability. For example, an indicator may fill in uniformly, but with increasing intensity, as the SPDi index increases. In an embodiment, the indicator 600 may have states that resemble different values on a grayscale, with the percentage grayscale increasing at the SPDi index increases.

A filled state of the graphical indicator 600 may trigger a primary or secondary alarm. In an embodiment, a primary alarm, such as a text alert, may be triggered when the graphical indicator 600 begins to fill. When the indicator 600 has reached a full state, a secondary alarm, such as an audio alarm, may then be triggered.

Figure 12:
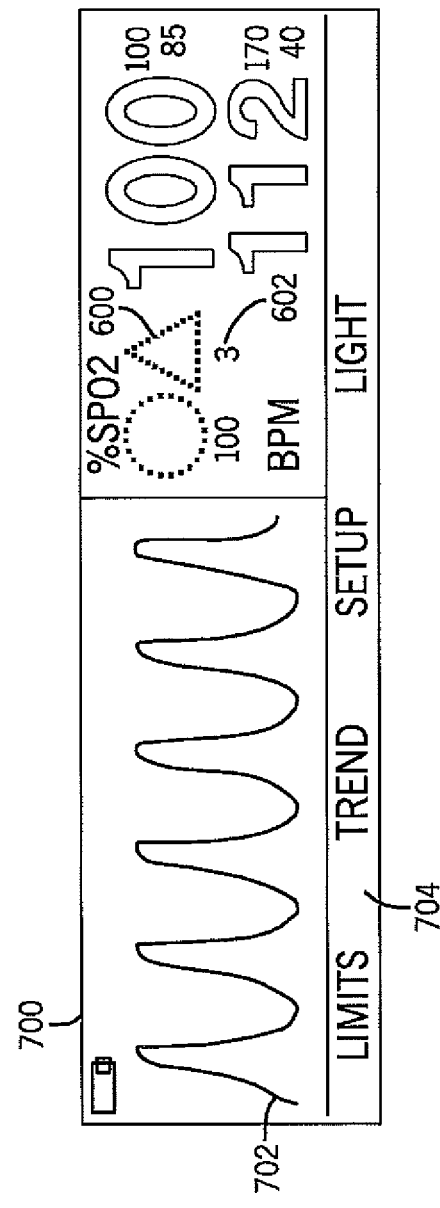
FIG. 12 is an exemplary display including a graphical indicator related to ventilatory instability.

The indicator 600 may be displayed on any number of monitor views to provide information to a healthcare provider during various monitoring activities. FIG. 12 shows an exemplary general pleth display 700 with a plethysmographic waveform 702. The display 700 may include a graphical indicator 600 for saturation pattern detection with a tolerance indicator 602. The display may also include softkeys 704 for navigating between other display views.

Figure 13:
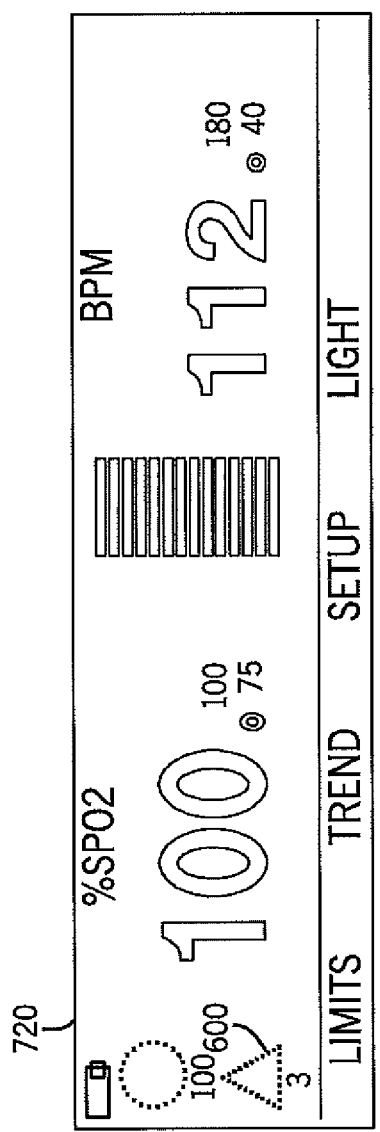
FIG. 13 is an exemplary display including a graphical indicator related to ventilatory instability.
Figure 14:
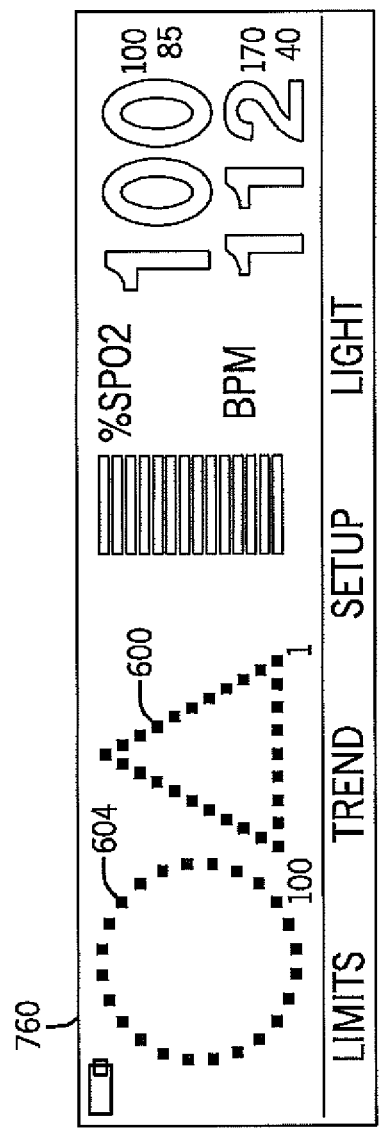
FIG. 14 is an exemplary display including a graphical indicator related to ventilatory instability.
Figure 15:
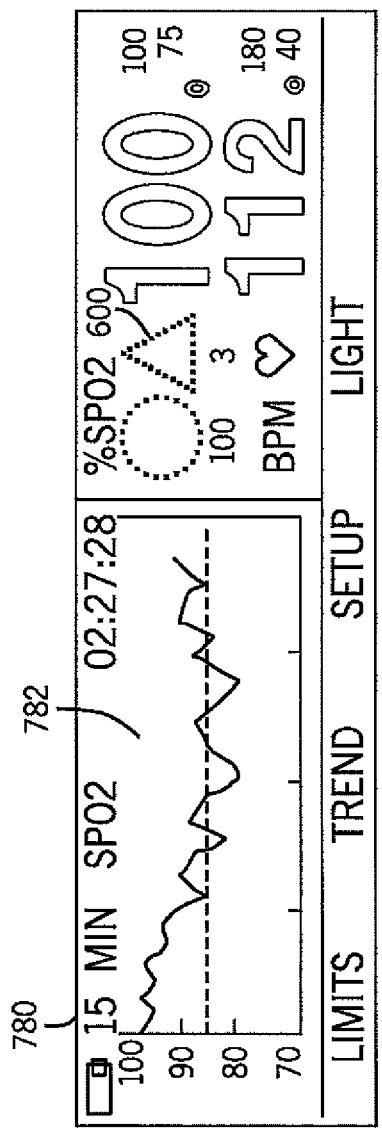
FIG. 15 is an exemplary display including a graphical indicator related to ventilatory instability.
Figure 16:
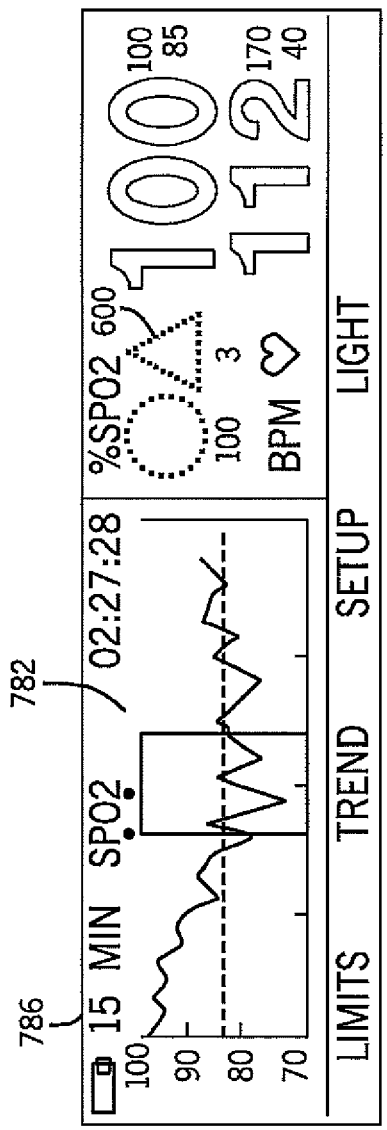
FIG. 16 is an exemplary display including a graphical indicator related to ventilatory instability.

FIG. 13 shows an exemplary blip display 720. As shown, the location of the graphical indicator 600 on the screen may change according to the particular display view chosen. However, the general shape of the indicator 600 may remain substantially the same so that the user may easily identify the indicator 600. FIG. 14 shows an exemplary general care format view 760. As shown, the graphical indicator 600 and the Sat Seconds indicator 604 may be relatively larger in certain views. FIG. 15 shows a real-time trend display 780 with a trend xy plot 782. FIG. 16 shows a display 786 in which an SPD event 788 is highlighted on the xy plot 782. In FIG. 15 and FIG. 16, the graphical indicator 600 may be displayed along with other indicators and patient data.

In embodiments, a user may have the ability to change certain settings on the monitor 10 related to the graphical indicator 600. In one embodiment, a user may be able to change settings related to SPD alarm limits. An alarm setup display related to the SPD alarm settings may be accessed via softkey from other display screens. FIG. 17 is an exemplary alarm setup display 800. As shown, a user may be able to select an option in which the monitor 10 activates SPD calculation features and associated indicators and alarms. In addition, a user may activate a Sat Seconds calculation and/or display feature. In an embodiment, a user may be able to select between audio and/or visual alarms in response to saturation pattern detection by the monitor 10, as shown in FIG. 18, which depicts a display 820 in which a user may select to turn off audio alerts related to saturation pattern detection.

Figure 19:
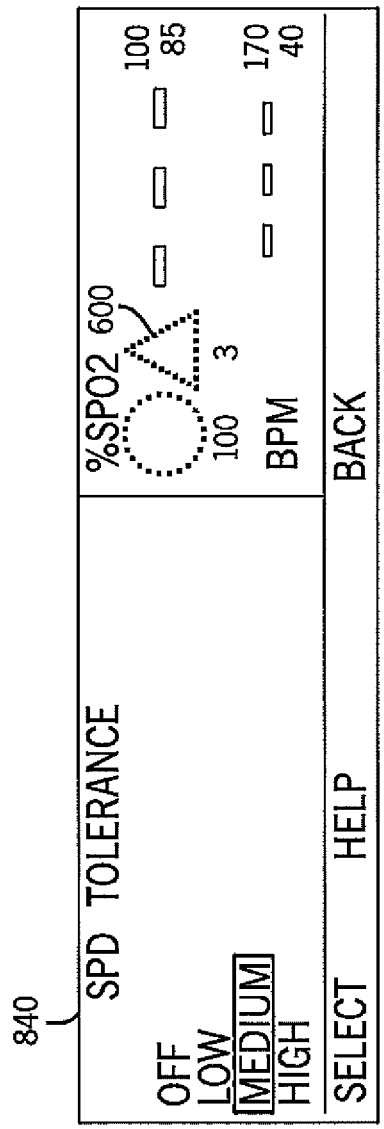
FIG. 19 is an exemplary display of a menu related to alarm management and settings for alarms related to ventilatory instability.

In another embodiment, a user may be able to change the default values on the limits to user-selected values. FIG. 19 is an exemplary display 840 showing an SPD Tolerance menu. A user may select between multiple SPD tolerance settings for High, Medium, or Low Tolerance of the SPD-associated alarms. In an embodiment, a monitor 10 may store certain default values associated with SPDi index values. These default values may be determined based on clinical observations of a test patient population or other input from healthcare providers. For example, the default High Tolerance value may be associated with an SPDi index value of 24. Accordingly, any SPD-associated alarms may not trigger until the SPDi index for a calculated window of time is at or near 24.

In another embodiment, a user may input specific values for High, Medium, and Low Tolerance limits. A user may select any value, so long as the High Tolerance limit is higher than the Medium Tolerance limit, and the Medium Tolerance limit is higher than the Low Tolerance limit. A monitor 10 may be able trigger an error message if a user attempts to set a limit of less than zero or if a user attempts to set a High Tolerance limit that is lower than a Medium Tolerance limit, and so on.

FIG. 20 is a flow chart 900 indicating how a monitor 10 may trigger alarms based on the SPDi tolerance settings. At start 902, if a tolerance setting is set to "OFF" at 904, the process sets the alarm status to "NO SPD ALARM" at 905. If the tolerance is set to Low (906), Medium (908), or High (910), the SPDi index is compared to the appropriate threshold, depending on the setting. For example, if the tolerance is set to Low at 906, the SPDi index is compared to the Low Index Limit at 912. If the SPDi index is lower that the Low Index Limit, the process may set the alarm status to "NO SPD ALARM" at 905. If the SPDi index is higher than the Low Index Limit, the process may then determine if audio alerts have been enabled at 914. If such alerts have not been enabled, the process set the alarm status to "VISUAL ONLY" to trigger visual alarms at 916. If audible alerts have been enabled, the alarm status may be set to "AUDIBLE VISUAL" at 918 for triggering audible and visual alarms before the process ending at 920. Similarly, a Medium Tolerance setting may be compared to a Medium Index Limit at 922 and a High Tolerance setting may be compared to a High Index Limit at 924.

While the embodiments of the present disclosure may be susceptible to various modifications and alternative forms, specific embodiments have been shown by way of example in the drawings and will be described in detail herein. However, it should be understood that the present embodiments are not intended to be limited to the particular forms disclosed. Rather, present embodiments are to cover all modifications, equivalents and alternatives falling within the spirit and scope of present embodiments as defined by the following appended claims.

What is claimed is:

1. A monitoring system, comprising:
a monitor capable of receiving input relating to patient physiological parameters and storing data related to the parameters, the monitor comprising:
a pattern detection feature capable of analyzing the data to detect a pattern in the data, wherein the analyzing comprises detecting a fall peak, a nadir peak, and a rise peak in the data, which, in sequence, define a reciprocation;
a pattern qualification feature capable of determining if the detected pattern is due to a ventilatory instability; and
a graphical indicator capable of being displayed comprising a graphical representation based at least in part on a magnitude of the pattern.

2. The system of claim 1, wherein data related to the parameters comprises pulse oximtery data.

3. The system of claim 1, wherein the graphical indicator comprises an indicator that changes in relation to the magnitude of the pattern.

4. The system of claim 1, wherein the graphical indicator comprises a geometric shape and wherein the geometric shape is filled in relation to the magnitude of the pattern.

5. The system of claim 1 further comprising an index calculation feature capable of determining a scoring metric associated with the pattern.

6. The system of claim 5, wherein the graphical indicator changes in relation to the scoring metric calculated over time.

7. The system of claim 5, further comprising an alarm that is triggered when the scoring metric reaches a predetermined threshold.

8. The system of claim 7, wherein the predetermined threshold may be selected by a user.

9. The system of claim 7, wherein the predetermined threshold may be selected from a high tolerance, medium tolerance, and low tolerance threshold.

10. The system of claim 1, wherein the graphical indicator comprises a graphic triangle capable of filling from the bottom of the triangle to the top of the triangle as an SPDi value increases.

11. A method, comprising:
- receiving, by a patient monitor, input relating to patient physiological parameters and storing data related to the parameters;
- detecting, by the patient monitor, an oxygen desaturation pattern indicative of ventilatory instability in the data, wherein the detecting comprises detecting a fall peak, a nadir peak, and a rise peak in the data, which, in sequence, define a reciprocation; and
- qualifying, by the patient monitor, the detected pattern by determining if the detected pattern is due to a ventilatory instability.

12. The method of claim 11, further comprising displaying a graphical indicator comprising a graphical representation based at least in part on a magnitude of the oxygen desaturation pattern indicative of ventilatory instability.

13. The method of claim 12, further comprising filling the graphical indicator based at least in part on the magnitude of the oxygen desaturation pattern indicative of ventilatory instability.

14. The method of claim 11, further comprising determining a scoring metric associated with the detected oxygen desaturation pattern indicative of ventilatory instability.

15. The method of claim 14, further comprising triggering an alarm when the scoring metric reaches a predetermined threshold.

16. The method of claim 15, further comprising receiving input to set the predetermined threshold.

17. The method of claim 15, wherein the predetermined threshold comprises a high tolerance threshold, a medium tolerance threshold, or a low tolerance threshold.

18. A system, comprising:
- a monitor capable of receiving input from a sensor related to patient physiological parameters and storing the data related to the parameters, the monitor comprising:
  - a pattern detection feature capable of analyzing the data to detect a pattern in the data, wherein the analyzing comprises detecting a fall peak, a nadir peak, and a rise peak in the data, which, in sequence, define a reciprocation;
  - a pattern qualification feature capable of determining if the detected pattern is due to a ventilatory instability; and
  - a graphical indicator capable of being displayed comprising a graphical representation based at least in part on the magnitude of the pattern.

19. The system of claim 18, wherein the sensor comprises a pulse oximetry sensor.

20. The system of claim 18, wherein the monitor further comprises an alarm capable of being triggered when the graphical indicator is empty or full.

* * * * *